United States Patent [19]

Tsuji et al.

[11] Patent Number: 4,877,876
[45] Date of Patent: Oct. 31, 1989

[54] NOVEL INDENOTHIAZOLE DERIVATIVE AND PROCESS FOR PREPARING THE SAME

[75] Inventors: Masayoshi Tsuji; Akira Nakagawa, both of Tosu; Hisataka Inoue, Okawa; Terumi Hachiya, Kanzaki; Yoshihiro Tanoue, Chikushi; Kouichi Ikesue, Saga; Masaru Saita, Miyaki; Takenobu Mizoguchi, Tosu; Testsuo Aoki; Hironobu Sato, both of Miyaki; Kanji Nodo, Chikushino

[73] Assignee: Hisamitsu Pharmaceutical Co., Inc., Tosu, Japan

[21] Appl. No.: 107,600
[22] PCT Filed: Jan. 14, 1987
[86] PCT No.: PCT/JP87/00021
§ 371 Date: Aug. 31, 1987
§ 102(e) Date: Aug. 31, 1987
[87] PCT Pub. No.: WO87/04434
PCT Pub. Date: Jul. 30, 1987

[30] Foreign Application Priority Data

Jan. 16, 1986 [JP] Japan ............... 61-7640

[51] Int. Cl.⁴ ............... C07D 277/60; C07D 417/12
[52] U.S. Cl. ............... 544/133; 544/368; 546/198; 546/270; 548/150
[58] Field of Search ............ 548/150; 546/198, 270; 544/133, 368

[56] References Cited

U.S. PATENT DOCUMENTS 4,082,773  4/1978  Hauck ............... 548/150

FOREIGN PATENT DOCUMENTS 44443  1/1982  European Pat. Off. ............ 548/150

Primary Examiner—Robert Gerstl
Attorney, Agent, or Firm—Bucknam and Archer

[57] ABSTRACT

This invention provides an indenothiazole derivative and a process for manufacturing the same. The said indenothiazole derivative is represented by the following formula:

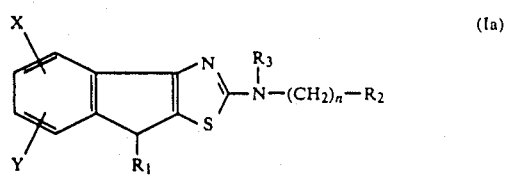

(Ia)

wherein X and Y are identical with, or different from, each other and are each a hydrogen atom, halogen atom, low alkyl group or low alkoxy group; n is an integer of from 0 to 4; $R_1$ is a hydrogen atom, low alkyl group, unsubstituted or substituted phenyl group; $R_2$ is a low alkyl group, cycloalkyl group, low alkoxyl group, unsubstituted or substituted phenoxy group, unsubstituted or substituted phenyl group, alkenyl group, heterocyclic group or cycloamino group; $R_3$ is a hydrogen atom, low alkyl group or acyl group; and $R_2$ and $R_3$ may be combined to form a cycloamino group. Further, this invention also provides a tautomer of the compound represented by the above formula (Ia), wherein all the symbols are as defined above except that $R_3$ is limited to a hydrogen atom.

6 Claims, No Drawings

NOVEL INDENOTHIAZOLE DERIVATIVE AND PROCESS FOR PREPARING THE SAME

FIELD OF THE INVENTION

This invention relates to a novel indenothiazole derivative useful as a medicine having an excellent antiulcerative effect, and a process for preparing the same.

DESCRIPTION OF THE PRIOR ART

With regard to indenothiazole derivative, a process for manufacturing a 2-amino indenothiazole derivative is disclosed in Journal of the American Chemical Society, 72, 3722 (1950) and Journal of the Chemical Society 2740 (1958). Further, a process for manufacturing a 2-aminoacyl indenothiazole derivative and its potential as a medicine for curing allergic diseases are disclosed in Japanese Patent Appln. Laid-Open Gazette No. 58-55474. However, the indenothiazole derivative of this invention is neither disclosed nor suggested in any one of the aforesaid publications. Further, whether its tautomer exists is not known at all. Still further, it was of course unknown whether the indenothiazole derivative has an antiulcerative effect.

The medical treatment of digestive ucler seeks to restrain the attack factor and strengthen the defense factor. In recent years, in order to restrain the attack factor, a histamine $H_2$-antagonist such as cimetidine, ranitidine or famotidine plays the main role as a remedial medicine for ulcer. Nevertheless, the problem of relapse of ulcer remains unsolved. Further, omeprazole serving as an ATPase inhibitor (or a proton pump inhibitor) restrains acid secretion and has a high selectivity for internal organs. It has a stable effect over a long period, but has a problem as to its side effects.

As for reinforcing agents for the defense factor, there are plenty of medicines which have the actions of strengthening of mucous membrane resistance, promoting mucus secretion, improving minute circulations and promoting prostagrandine synthesis. Although these medicines have so minor side effects that they are safely used, they are still not appreciated to be sufficiently effective.

It is an object of this invention to provide a novel indenothiazole derivative, a tautomer thereof or their acid addition salt, which is a useful medicine having an excellent antiulcerative effect with no side actions.

It is another object to provide a process for preparing the novel indenothiazole derivative, the tautomer thereof or their acid addition salt.

DISCLOSURE OF THE INVENTION

The novel indenothiazole derivative is represented by the following formula:

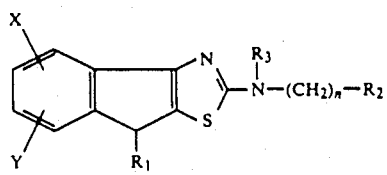

(Ia)

wherein X and Y are identical with, or different from, each other and are each a hydrogen atom, halogen atom, lower alkyl group or lower alkoxy group; n is an integer of 0 to 4; $R_1$ is a hydrogen atom, lower alkyl group, unsubstituted or substituted phenyl group; $R_2$ is a lower alkyl group, cycloalkyl group, low alkoxy group, unsubstituted or substituted phenoxy group, unsubstituted or substituted phenyl group, alkenyl group, heterocyclic group or cyclic amino group; $R_3$ is a hydrogen atom, lower alkyl group or acyl group; $R_2$ and $R_3$ may be combined together to form a cyclic amino group.

Further, the tautomer is represented by the following formula:

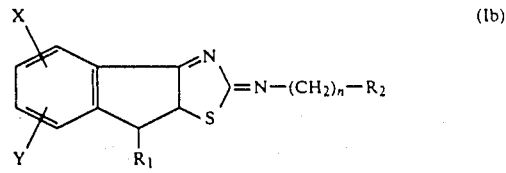

(Ib)

wherein X, Y, n, $R_1$ and $R_2$ are as defined above.

The compounds of the aforesaid formulas (Ia) and (Ib) are described hereinafter in more detail.

The halogen atom means a fluorine, chlorine, bromine or iodine atom. The lower alkyl group includes an alkyl group of 1 to 6 carbon atoms such as methyl, ethyl, n-propyl, iso-propyl, n-butyl, iso-butyl, tert.-butyl, n-pentyl, iso-pentyl or n-hexyl group.

The cycloalkyl group includes a cycloalkyl group having 3 to 7 carbon atoms such as cyclopropyl, cyclopentyl, cyclohexyl or cycloheptyl group.

The lower alkoxy group includes an alcoxy group having 1 to 6 carbon atoms such as methoxy, ethoxy, n-propoxy, iso-propoxy, n-butoxy, iso-butoxy or tert.-butoxy group.

The substituent in the substituted phenyl or substituted phenoxy group includes a halogen atom, lower alkyl group (this group may further contain mono- or di-$C_{1-6}$ alkylamino group as a substituent), hydroxyl group, lower alkoxy group or trifluoromethyl group.

The alkenyl group includes an alkenyl group having 3 to 6 carbon atoms such as propenyl, butenyl or butadienyl group.

The heterocyclic group includes 2-pyridyl, 3-pyridyl, 4-pyridyl, 2-pyrimidyl, 2-thiazolyl, 2-thiazoline-2-yl or 2-thiazolydinyl group, each of which may be unsubstituted or substituted with the same substituent as in the above phenyl or phenoxy group.

The cycloamino group includes a 5- or 6-membered cycloamino group which may have nitrogen atoms or oxygen atoms, such as piperidino, pyrrolidino, morpholino, piperazino or pipecolino group. Further, the cycloamino group may be substituted by an alkyl group of 1 to 4 carbon atoms such as methyl or ethyl group, a phenyl-$C_{1-4}$ alkyl group such as benzyl group, an alkanoyl group of 2 to 6 carbon atoms such as acetyl or propionyl group.

The acyl group includes an alkanoyl group of 2 to 6 carbon atoms such as acetyl, propionyl, n-butyroyl or isobutyroyl group, benzoyl group or trifluoromethylcarbonyl group.

The acid addition salt, which is permissible as a medicine, comprises an acid of equivalent 1 or 2. The suitable acid may for example be an inorganic acid such as hydrochloric, sulfuric, nitric or phosphoric acid as well as an organic acid such as maleic, fumaric, oxalic, succinic, malonic, lactic or citric acid.

In cases where the compounds represented by the aforesaid formulas (Ia) and (Ib) or their acid addition salts are used as a medicine, they may stably be orally or non-orally administered as they are or in the form of tablets, powders, capsules or suppositories prepared using a known vehicle as well as in the form of injections. The suitable dosage may be decided in view of a patient's symptoms, age, sex or the like. In cases where they are orally dosed as a medicine to cure gastric ulcer, duodenal ulcer or acute or chronic gastritis, it is desirable to dose the compound represented by the aforesaid formulas (Ia) or (Ib) or its acid addition salt in an amount of about 1 to 200 mg/kg at a time, about once or three times per day.

The process of manufacturing the compounds of this invention will be described hereinafter. The present compounds may be obtained in a good yield as indicated by the following embodiments, but this invention is not limited to them.

The starting or raw materials represented by the following formulas may be easily synthesized by the known processes disclosed in Journal of the American Chemical Society, 71, 1092 (1949), Journal of the American Chemical Society, 75, 640 (1953), Journal Für Praktische Chemie, 315, 144 (1973), Russian Chemical Reviews, 42 (7), 587 (1973), Journal of the Chemical Society, 2740 (1958) and so forth.

temperature of 20° to 120° C., in any one of the organic solvents such as methanol, ethanol, acetone or dimethylformamide, so as to obtain a compound represented by the formula (Ia). Further, the compound represented by the formula (Ia) in which $R_3$ is hydrogen atom is treated in an aqueous solution of an acid, so as to obtain its tautomer, i.e. the compound represented by the formula (Ib).

Manufacturing process 2

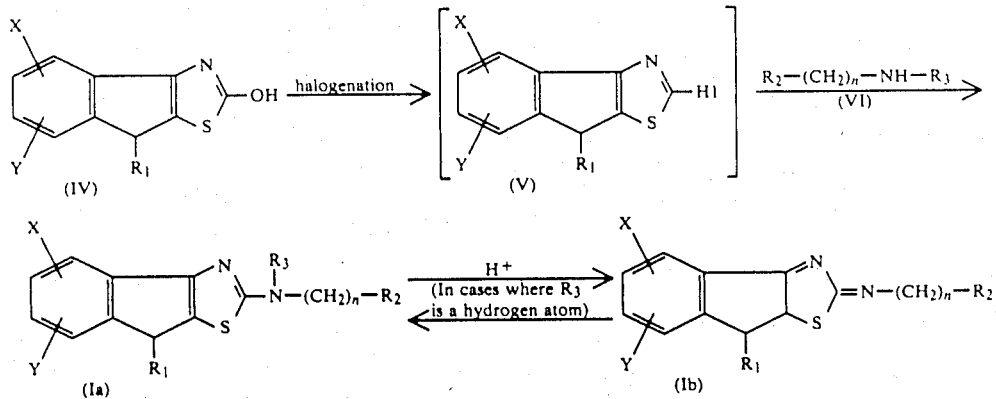

(Wherein X, Y, n, $R_1$, $R_2$ and $R_3$ respectively have the same meaning as described above; and Hl is a halogen atom.)

First, a compound represented by the formula (IV) is halogenated by reacting with a halogenating agent such as thionyl chloride or phosphorus oxychloride, for 1 to 5 hours at a temperature of 0° to 120° C., in the absence or presence of an aprotic solvent such as benzene or toluene. Thereafter, the thus obtained halogenated compound is reacted with an amine represented by the formula (VI) for 1 to 5 hours at a temperature of 20° to 100° C., in the absence or presence of an organic solvent such as methanol, ethanol or dimethylformamide, thereby to obtain the compound represented by the formula (Ia). Further, it is possible to obtain the tautomer (Ib) of the compound (Ia) in which $R_3$ is a hydrogen atom by means of the aforesaid manufacturing process 1.

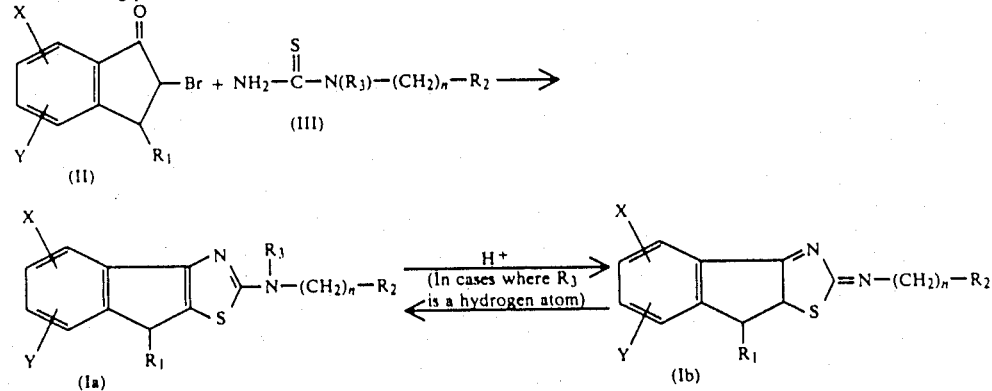

(Wherein X, Y, n, $R_1$, $R_2$ and $R_3$ respectively have the same meaning as previously defined.)

As indicated above, a compound represented by the above formula (II) and a compound represented by the above formula (III) are reacted, for 1 to 24 hours at a

EXAMPLES

Examples of this invention are described hereinafter, but this invention is not limited to them.

Example 1

3.5 g of 2-bromo-5-fluoro-1-indanone and 3.1 g of N-(3-morpholinopropyl)thiourea were added to 40 ml of ethanol. The resulting mixture was refluxed for 10 minutes, agitated for 24 hours at room temperature to precipitate crystals which were collected by filtration. The thus collected crystals were washed with ethanol, dried, incorporated with 40 ml of a 5% aqueous solution of NaOH, extracted with ethyl acetate, washed with water, dried, distilled at a reduced pressure and then recrystallized from ethyl acetate-isopropyl ether thereby to obtain 3.9 g of 2-(3-morpholinopropyl)amino-6-fluoro-8H-indeno[1.2-d]thiazole. The thus obtained compound had a melting point of 113° to 115° C. and the following analysis.

| Analysis: $C_{17}H_{20}N_3OFS$ | | | |
|---|---|---|---|
| Calculated | C: 61.24 | H: 6.04 | N: 12.60 |
| Found | C: 61.00 | H: 6.04 | N: 12.47 |

Example 2

3.0 g of 2-(3-morpholinopropyl)amino-6-fluoro-8H-indeno[1.2-d]thiazole were dissolved in 50 ml of 0.1N HCl, allowed to stand for three days at room temperature, made weakly alkaline with a 5% KOH aqueous solution, extracted with chloroform, water washed, dried, distilled at a reduced pressure to remove the solvent, and then isolated and purified by silica gel column chromatography in which a developing solvent consisting of chloroform, methanol and ammonia water in a ratio of 10:1:0.1 was used, thereby to obtain 1.0 g of a tautomer having the following formula:

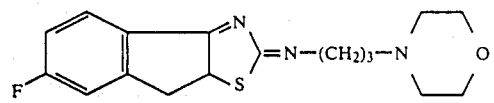

The compound so obtained also exhibited the following characteristics:

Infrared rays absorption spectra [KBr method, cm$^{-1}$] 3270, 1600, 1485, 1250, 1115, 1065, 860, 755

Nuclear magnetic resonance spectra (DMSOd$_6$, δ value, ppm) 1.59 (q, 2H), 2.24 (t, 4H), 2.28 (t, 2H), 2.83 and 3.50 (dd, 2H), 3.13 (t, 2H), 3.54 (t, 4H), 4.15 (dd, 1H), 6.98 (dd, 1H), 7.03 (td, 1H), 7.35 (dd, 1H)

Examples 3 to 129

The compounds represented by the formula (Ia) were prepared in the same manner as in Example 1 (Examples 3 to 122). The substituents in the compounds and the melting points of the compounds are shown in Tables 1 and 2.

The compounds represented by the formula (Ib) were prepared in the same manner as in Example 2 (Examples 123 to 129). The substituents in the compounds and the results of infrared spectrography are shown in Table 3.

TABLE 1

| Example No. | X, Y | n | R$_1$ | R$_2$ | R$_3$ | Melting Point (°C.) |
|---|---|---|---|---|---|---|
| 3 | H | 0 | H | —CH$_3$ | H | 188–189 |
| 4 | 5-Cl | 0 | H | —CH$_3$ | H | 225–227 |
| 5 | 6-Cl | 0 | H | —CH$_3$ | H | 250 (dec.) |
| 6 | 7-Cl | 0 | H | —CH$_3$ | H | 226–227 |
| 7 | H | 1 | H | —CH(CH$_3$)$_2$ | H | 135–136 |
| 8 | 5-Cl | 1 | H | —CH(CH$_3$)$_2$ | H | 172–173 |
| 9 | 6-Cl | 1 | H | —CH(CH$_3$)$_2$ | H | 178–179 |
| 10 | 7-Cl | 1 | H | —CH(CH$_3$)$_2$ | H | 141–143 |
| 11 | 5-F | 1 | H | —CH(CH$_3$)$_2$ | H | 150–151 |
| 12 | H | 0 | H | —⬡ (cyclohexyl) | H | 114–115 |
| 13 | 5-Cl | 0 | H | —⬡ (cyclohexyl) | H | 160–161 |
| 14 | 6-Cl | 0 | H | —⬡ (cyclohexyl) | H | 140–141 |
| 15 | 7-Cl | 0 | H | —⬡ (cyclohexyl) | H | 220–222 |

TABLE 1-continued
| Example No. | X, Y | n | R₁ | R₂ | R₃ | Melting Point (°C.) |
|---|---|---|---|---|---|---|
| 16 | 5-F | 0 | H | 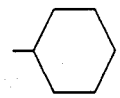 | H | 181–182 |
| 17 | H | 0 | H | 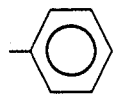 | —CH₃ | 230 (dec.: decomposition) |
| 18 | 5-Cl | 0 | H | 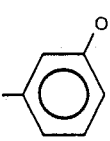 | H | 209–210 |
| 19 | 7-Cl | 0 | H | 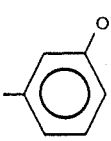 | H | 245–247 |
| 20 | 7-Cl | 0 | H | 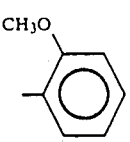 | H | 160–162 |
| 21 | 7-Cl | 0 | H | 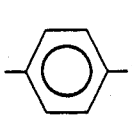 | H | 178–179 |
| 22 | 7-Cl | 0 | H | 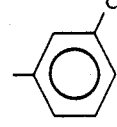 | H | 178–179 |
| 23 | 5-Cl | 0 | H | 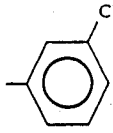 | H | 188–189 |
| 24 | 5-Cl | 0 | H | 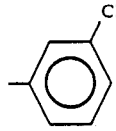 | H | 174–175 |
| 25 | H | 0 | H | 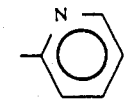 | H | 240–241 |
| 26 | 5-Cl | 0 | H | 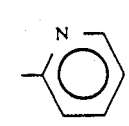 | H | 267 (dec.) |
| 27 | 6-Cl | 0 | H | 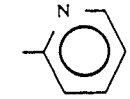 | H | 270 (dec.) |

TABLE 1-continued
| Example No. | X, Y | n | R₁ | R₂ | R₃ | Melting Point (°C.) |
|---|---|---|---|---|---|---|
| 28 | 7-Cl | 0 | H | 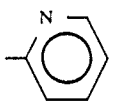 | H | 270 (dec.) |
| 29 | 5-F | 0 | H | 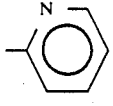 | H | 261-264 |
| 30 | 7-F | 0 | H | 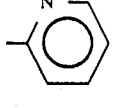 | H | 265-269 |
| 31 | 5-CH₃ | 0 | H | 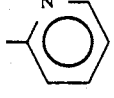 | H | 224-226 |
| 32 | 5-CH(CH₃)₂ | 0 | H | 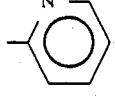 | H | 238-240 |
| 33 | H | 0 | —CH₃ | 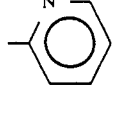 | H | 207-209 |
| 34 | 7-Cl | 0 | H | 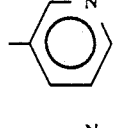 | H | 270 (dec.) |
| 35 | 5-F | 0 | H | 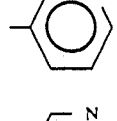 | H | 278 (dec.) |
| 36 | 7-F | 0 | H | 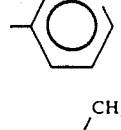 | H | 266 (dec.) |
| 37 | 7-Cl | 0 | H | 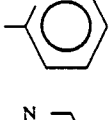 | H | 278 (dec.) |
| 38 | 7-Cl | 0 | H | 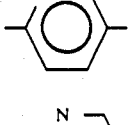 | H | 280 (dec.) |
| 39 | 7-Cl | 0 | H | 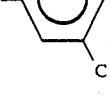 | H | 256-260 |

TABLE 1-continued

| Example No. | X, Y | n | R₁ | R₂ | R₃ | Melting Point (°C.) |
|---|---|---|---|---|---|---|
| 40 | 7-Cl | 0 | H | 3-methylpyridin-2-yl | H | 194–197 |
| 41 | 7-Cl | 0 | H | 2,4-dimethylpyridin-6-yl | H | 270 (dec.) |
| 42 | 7-Cl | 0 | H | 4-ethylpyridin-2-yl | H | 227–230 |
| 43 | 7-F | 0 | H | 2-methylpyridin-6-yl | H | 250–254 |
| 44 | 7-F | 0 | H | 4-methylpyridin-2-yl | H | 263–266 |
| 45 | 7-F | 0 | H | 4-methylpyridin-2-yl | H | 257–261 |
| 46 | 7-F | 0 | H | 2,4-dimethylpyridin-6-yl | H | 270 (dec.) |
| 47 | 7-Cl | 1 | H | pyridin-2-yl | H | 125–127 |
| 48 | 7-Cl | 2 | H | pyridin-2-yl | H | 190–194 |
| 49 | 7-Cl | 2 | H | pyridin-2-yl | —COCH₃ | 168–169 |
| 50 | 7-Cl | 0 | H | —CH₂—CH=CH₂ | H | 178–180 |

TABLE 1-continued
| Example No. | X, Y | n | R₁ | R₂ | R₃ | Melting Point (°C.) |
|---|---|---|---|---|---|---|
| 51 | 5-Cl | 0 | H |  | H | 290 dec. |
| 52 | 6-F | 2 | H | 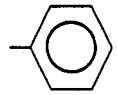 | H | 154–156 |
| 53 | 6-F | 2 | H | 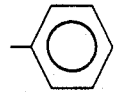 | —COCH₃ | 153–154 |
| 54 | 7-Cl | 1 | H | 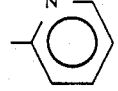 | —COCH₃ | 180–181 |
| 55 | H | 3 | H | —O—CH(CH₃)₂ | H | 108–111 |
| 56 | 7-Cl | 0 | H | 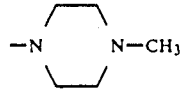 | H | 178–180 |
| 57 | H | 2 | H | 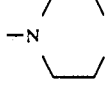 | H | 112–114 |
| 58 | H | 2 | H | 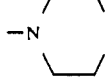 | —COCH₃ | 173–175 |
| 59 | 5-Cl | 2 | H | 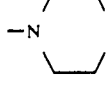 | H | 159–161 |
| 60 | 7-Cl | 2 | H | 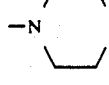 | H | 153–155 |
| 61 | H | 3 | H | 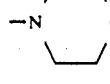 | H | 104–106 |
| 62 | H | 3 | H | 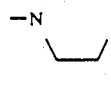 | —COCH₃ | 126–128 |
| 63 | 5-Cl | 3 | H | 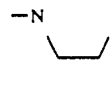 | H | 127–128 |
| 64 | 6-Cl | 3 | H | 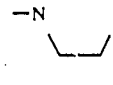 | H | 106–108 |

TABLE 1-continued
| Example No. | X, Y | n | R₁ | R₂ | R₃ | Melting Point (°C.) |
|---|---|---|---|---|---|---|
| 65 | 6-Cl | 3 | H | 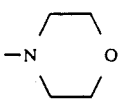 | —COCH₃ | 138–140 |
| 66 | 7-Cl | 3 | H | 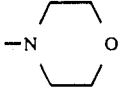 | H | 103–104 |
| 67 | 7-Cl | 3 | H | 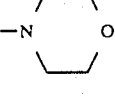 | —COCH₃ | 180–182 |
| 68 | 5,7-diCl | 3 | H | 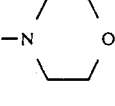 | H | 113–114 |
| 69 | 5-F | 3 | H | 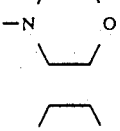 | H | 104–106 |
| 70 | 6-F | 3 | H | 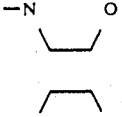 | —COCH₃ | 144–146 |
| 71 | 7-F | 3 | H | 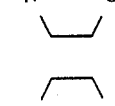 | H | 123–125 |
| 72 | 5-CH₃ | 3 | H | 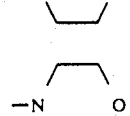 | H | 125–127 |
| 73 | 7-CH₃ | 3 | H | 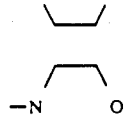 | H | 120–122 |
| 74 | 5-CH(CH₃)₂ | 3 | H | 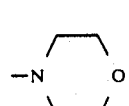 | H | 141–143 |
| 75 | 5-CH(CH₃)₂ | 3 | H | 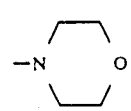 | —COCH₃ | 155–157 |
| 76 | 5-CH(CH₃)₂ | 3 | H | 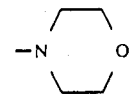 | —COCF₃ | 85–87 |
| 77 | 5-OCH₃ | 3 | H |  | H | normally oily |

TABLE 1-continued

| Example No. | X, Y | n | R₁ | R₂ | R₃ | Melting Point (°C.) |
|---|---|---|---|---|---|---|
| 78 | 6-OCH₃ | 3 | H | —N(morpholino) | H | normally oily |
| 79 | 5,6-di-OCH₃ | 3 | H | —N(morpholino) | H | normally oily |
| 80 | H | 3 | —CH₃ | —N(morpholino) | H | normally oily |
| 81 | H | 3 | —CH₃ | —N(morpholino) | —COCH₃ | 83–85 |
| 82 | 6-Cl | 3 | —CH₃ | —N(morpholino) | H | normally oily |
| 83 | 7-Cl | 3 | —CH₃ | —N(morpholino) | H | normally oily |
| 84 | 7-F | 3 | —CH₃ | —N(morpholino) | H | normally oily |
| 85 | 5,7-diCl | 3 | —CH₃ | —N(morpholino) | H | normally oily |
| 86 | H | 3 | —C₂H₅ | —N(morpholino) | H | normally oily |
| 87 | H | 3 | —(CH₂)₂CH₃ | —N(morpholino) | H | normally oily |
| 88 | H | 3 | —CH(CH₃)₂ | —N(morpholino) | H | normally oily |
| 89 | H | 3 | —(CH₂)₄CH₃ | —N(morpholino) | H | normally oily |
| 90 | H | 3 | —C₆H₅ | —N(morpholino) | H | normally oily |

TABLE 1-continued
| Example No. | X, Y | n | R₁ | R₂ | R₃ | Melting Point (°C.) |
|---|---|---|---|---|---|---|
| 91 | H | 3 | H | 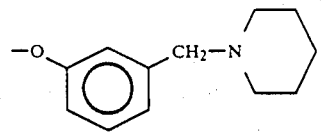 | H | 111–113 |
| 92 | H | 4 | H | 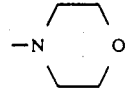 | H | 120–122 |
| 93 | H | 4 | H | 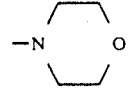 | —COCH₃ | 79–81 |
| 94 | 5-Cl | 4 | H | 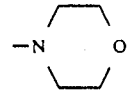 | H | 149–151 |
| 95 | 7-Cl | 4 | H | 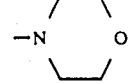 | H | 126–127 |
| 96 | H | 4 | —CH₃ | 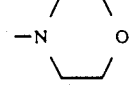 | H | normally oily |
| 97 | 7-Cl | 4 | —CH₃ | 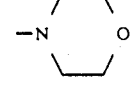 | H | normally oily |
| 98 | H | 2 | H | 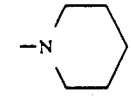 | H | 116–118 |
| 99 | H | 3 | H | 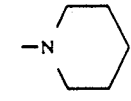 | H | 97–99 |
| 100 | H | 3 | H | 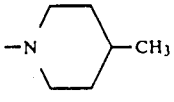 | H | 93–94 |
| 101 | H | 3 | H | 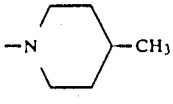 | —COCH₃ | 101–103 |
| 102 | H | 2 | H | 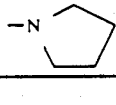 | H | 150–153 |

TABLE 2

| Example No. | X, Y | R₁ | −N(R₃)−(CH₂)ₙ−R₂ | Melting Point (°C.) |
|---|---|---|---|---|
| 103 | H | H | −N(pyrrolidine) | 113–114 |
| 104 | 5-Cl | H | −N(pyrrolidine) | 167–168 |
| 105 | 6-Cl | H | −N(pyrrolidine) | 150–151 |
| 106 | 7-Cl | H | −N(pyrrolidine) | 156–157 |
| 107 | 5-F | H | −N(pyrrolidine) | 123–124 |
| 108 | 5,7-diCl | H | −N(pyrrolidine) | 167–168 |
| 109 | 5-OCH₃ | H | −N(pyrrolidine) | 112–114 |
| 110 | 6-OCH₃ | H | −N(pyrrolidine) | 134–135 |
| 111 | 5,6-di-OCH₃ | H | −N(pyrrolidine) | 143–144 |
| 112 | H | H | −N(piperidine) | 74–75 |
| 113 | 5-Cl | H | −N(piperidine) | 112–113 |
| 114 | 6-Cl | H | −N(piperidine) | 91–93 |
| 115 | 7-Cl | H | −N(piperidine) | 128–129 |
| 116 | 5-F | H | −N(piperidine) | 98–99 |
| 117 | 5,7-diCl | H | −N(piperidine) | 141–142 |
| 118 | 5-OCH₃ | H | −N(piperidine) | 96–97 |
| 119 | 6-OCH₃ | H | −N(piperidine) | 82–83 |
| 120 | 5,6-di-OCH₃ | H | −N(piperidine) | 133–134 |
| 121 | 5-Cl | H | −N(morpholine) | 119–120 |
| 122 | 7-Cl | H | −N(3,5-dimethylpiperidine) | 151–153 |

TABLE 3

| Example No. | X, Y | n | R₁ | R₂ | Infrared Rays Absorption Spectra (KBr method, cm⁻¹) |
|---|---|---|---|---|---|
| 123 | 7-Cl | 1 | H | 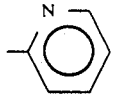 | 3180, 1605, 1440 1275, 1125, 1075 |

TABLE 3-continued

| Example No. | X, Y | n | R₁ | R₂ | Infrared Rays Absorption Spectra (KBr method, cm⁻¹) |
|---|---|---|---|---|---|
| 124 | 7-Cl | 1 | —CH₃ | 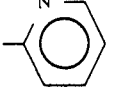 | 3180, 1605, 1435, 1245, 1130, 750 |
| 125 | 7-Cl | 2 | H | 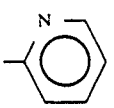 | 3220, 1600, 1430, 1250, 1120, 1090 |
| 126 | 5-CH(CH₃)₂ | 3 | H | 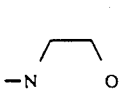 | 3150, 1610, 1490, 1270, 1230, 1120 |
| 127 | 6-Cl | 3 | H | 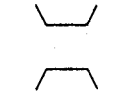 | 3280, 1610, 1220, 1115, 1070, 860 |
| 128 | 7-Cl | 2 | H | 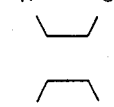 | 3400, 1610, 1225, 1115, 1065, 860 |
| 129 | H | 4 | H | 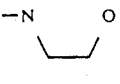 | 3180, 1610, 1450, 1250, 1115, 790 |

Pharmacological test

Groups each consisting of 9 to 10 Wistar-strained male rats, each weighing about 200 g, were used in the test after their abstinence from food and water for 24 hours. Each test compound of this invention was administered in an amount of 50 mg/kg and a comparative medicine, "Neuer" (tradename: produced by Daiichi Pharmaceutical Co., Ltd.; effective component: centraxate) in an amount of 300 mg/kg. Each of the test compounds was administered orally to each rat of a first group and the comparative medicine to each rat of a second group one hour before oral administration of 1 ml of pure ethanol per rat. One hour later, each rat was sacrificed by exsanguination and its stomach was enucleated and fixed with 10 ml of 70% ethanol for about 30 minutes. A 0.5% tragacanth solution was administered to each rat of a third group. The ulcer was measured for length with naked eyes, and the test groups of rats were measured for their respective ulcer inhibition ratios in comparison with that for the third group.

Both the test compounds and the comparative medicine were each suspended or dissolved in a 0.5% tragacanth gum saline solution for use in the test. Table 4 shows the ulcer inhibition ratios obtained by the use of each of the test compounds and the comparative medicine in comparison with that obtained by the use of the control solution.

Ulcer inhibition ratio =

$$\frac{\text{Ulcer index for third group} - \text{Ulcer index for first or second group}}{\text{Ulcer index for third (control) group}} \times 100(\%)$$

TABLE 4

| Test compounds | Ulcer inhibition ratio (%) |
|---|---|
| Final compound of Example 1 | 89.0 |
| Final compound of Example 1 (dihydrochloride) | 94.1 |
| Final compound of Example 1 (maleic acid salt) | 89.5 |
| Final compound of Example 2 | 93.5 |
| Final compound of Example 7 | 79.0 |
| Final compound of Example 59 | 85.0 |
| Final compound of Example 61 | 90.0 |
| Final compound of Example 74 | 93.6 |
| Final compound of Example 74 (dihydrochloride) | 95.3 |
| Final compound of Example 75 | 91.9 |
| Final compound of Example 83 (dihydrochloride) | 85.9 |
| Final compound of Example 92 | 83.4 |
| Control medicine (Neuer) | 81.5 |

Acute toxicity

Groups each consisting of five Wistar-strained male rats, each weighing about 150 g, were used in the test. After each of said test compounds was suspended in a physiological saline water, the suspension was orally or abdominally administered to each of the test rats. The rats so administered had been observed for 8 days to find the lethal dose (LD₅₀) with the result that the LD₅₀ of each test compound was at least 1000 mg/kg when orally administered and at least 300 mg/kg when abdominally administered.

Industrial Applicability

From the results of the aforesaid pharmacological tests for acute toxicity, it has been found that the compounds (Ia) and (Ib) of this invention and their acid addition salts have safe and remarkable antiulcerative effects with no side effects. Accordingly, when they are used for the medical treatment, prophylaxis and relapse prevention of ulcer, they will be appreciated to be enough efficacious as medicines.

What is claimed is:

1. An indenothiazole derivative of formula:

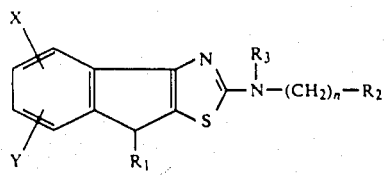

(Ia)

wherein X and Y are identical with, or different from, each other and are each hydrogen, halogen, lower alkyl having 1-6 carbon atoms or lower alkoxyl having 1-6 carbon atoms; n is an integer of from 0 to 4; $R_1$ is hydrogen, lower alkyl having 1-6 carbon atoms or phenyl; $R_2$ is lower alkyl having 1-6 carbon atoms, cyclohexyl, lower alkoxyl having 1-6 carbon atoms, alkenyl having 3-6 carbon atoms, phenyl, m-(1-piperidinylmethyl)-phenoxy, phenyl substituted by a halogen atom, hydroxyl, lower alkyl having 1-6 carbon atoms, lower alkoxyl having 1-6 carbon atoms or trifluoromethyl group, an heterocyclic ring selected from the group consisting of pyridyl, pyridyl mono- or di-substituted by one or two lower alkyl having 1-6 carbon atoms and thiazolyl and cycloamino selected from the group consisting of morpholino, piperidino, pyrrolidino, piperazino substituted by lower alkyl having 1-6 carbon atoms and piperidino substituted by lower alkyl having 1-6 carbon atoms; $R_3$ is hydrogen, lower alkyl having 1-6 carbon atoms, acetyl or trifluoromethylcarbonyl, or $R_2$ and $R_3$ are combined to form a cycloamino selected from the group consisting of pyrrolidino group, piperidino, morpholino and piperidino di-substituted by two lower alkyl having 1-6 carbon atoms.

2. An indenothiazole derivative of formula

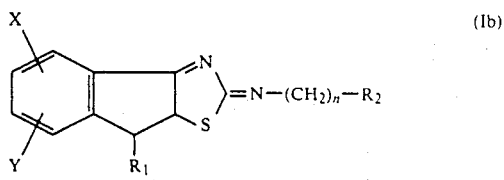

(Ib)

wherein X and Y are identical with, or different from, each other and are each hydrogen, halogen, lower alkyl having 1-6 carbon atoms or lower alkoxyl having 1-6 carbon atoms; n is an integer of from 0 to 4; $R_1$ is hydrogen, lower alkyl having 1-6 carbon atoms or phenyl; and $R_2$ is lower alkyl having 1-6 carbon atoms, cyclohexyl, lower alkoxyl having 1-6 carbon atoms, alkenyl having 3-6 carbon atoms, phenyl, m-(1-piperidinylmethyl)phenoxy group, phenyl group substituted by a halogen atom, hydroxyl, lower alkyl having 1-6 carbon atoms, lower alkoxyl group having 1-6 carbon atoms or trifluoromethyl, an heterocyclic group selected from the group consisting of pyridyl, pyridyl mono- or di-substituted by one or two lower alkyl having 1-6 carbon atoms and thiazolyl, and cycloamino selected from the group consisting of morpholino, piperidino, pyrrolidino, piperazino substituted by lower alkyl having 1-6 carbon atoms and piperidino substituted by lower alkyl having 1-6 carbon atoms.

3. An indenothiazole derivative according to claim 1, in which said heterocyclic group is 2-pyridyl group, 3-pyridyl group, 4-pyridyl group or 2-thiazolyl group.

4. An indenothiazole derivative according to claim 1, in which said indenothiazole derivative of the formula (Ia) is in the form of an acid addition salt.

5. An indenothiazole derivative according to claim 2, in which said indenothiazole derivative of the formula (Ib) is in the form of an acid addition salt.

6. An indenothiazole derivative according to claim 1, in which said halogen atom is fluorine, chlorine, bromine or iodine.

* * * * *